US007779003B2

(12) United States Patent
McKnight

(10) Patent No.: US 7,779,003 B2
(45) Date of Patent: Aug. 17, 2010

(54) COMPUTERIZED SEARCH SYSTEM FOR MEDICATION AND OTHER ITEMS

(75) Inventor: Lawrence McKnight, Chadds Ford, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 222 days.

(21) Appl. No.: 11/778,983

(22) Filed: Jul. 17, 2007

(65) Prior Publication Data

US 2008/0016042 A1 Jan. 17, 2008

Related U.S. Application Data

(60) Provisional application No. 60/807,514, filed on Jul. 17, 2006.

(51) Int. Cl.
*G06F 7/00* (2006.01)

(52) U.S. Cl. .................................... 707/728; 707/731

(58) Field of Classification Search .................. 707/3, 707/728, 731
See application file for complete search history.

(56) References Cited

U.S. PATENT DOCUMENTS

| 5,754,939 | A |   | 5/1998  | Herz et al.          |
|-----------|---|---|---------|----------------------|
| 5,867,799 | A | * | 2/1999  | Lang et al. ..... 1/1 |
| 6,065,001 | A |   | 5/2000  | Ohkubo et al.        |
| 6,082,776 | A | * | 7/2000  | Feinberg ..... 283/72 |
| 6,480,837 | B1|   | 11/2002 | Dutta                |
| 6,873,982 | B1|   | 3/2005  | Bates et al.         |
| 6,886,010 | B2| * | 4/2005  | Kostoff ..... 1/1    |
| 6,963,850 | B1|   | 11/2005 | Bezos et al.         |
| 7,181,438 | B1| * | 2/2007  | Szabo ..... 707/2    |
| 7,225,180 | B2|   | 5/2007  | Donaldson et al.     |
| 7,483,871 | B2| * | 1/2009  | Herz ..... 1/1       |
| 2003/0037041 | A1| * | 2/2003 | Hertz ..... 707/1   |
| 2006/0036619 | A1| * | 2/2006 | Fuerst et al. ..... 707/100 |
| 2006/0160074 | A1| * | 7/2006 | Dorn et al. ..... 435/6 |
| 2006/0248074 | A1| * | 11/2006 | Carmel et al. ..... 707/5 |
| 2006/0255136 | A1| * | 11/2006 | Wagner et al. ..... 235/385 |

OTHER PUBLICATIONS

Salton and Buckley, "Term Weighting Approaches in Automatic Text Retrieval," *Information Processing and Management*, (1988) 24:5 pp. 513-523.

* cited by examiner

*Primary Examiner*—James Trujillo
*Assistant Examiner*—Linh Black

(57) ABSTRACT

A search system finds an order to provide an item. The search system includes a repository including a plurality of records identifying a corresponding plurality of items for order. A record of an individual item for order includes a plurality of related text terms describing order related parameters. A search processor searches the plurality of records to find candidate items for order corresponding to a user entered search term by: identifying and prioritizing candidate items for order in response to a relative frequency of occurrence of the user entered search term in corresponding records of the candidate items for order; and ranking the identified and prioritized candidate items for order in response to a relative frequency of ordering of the identified and prioritized candidate items for use by users. An output processor provides search result data representing the ranked, identified and prioritized candidate items.

15 Claims, 3 Drawing Sheets

```
19   def lookup(self, searchString):
20         """returns a list of candidate items matching the user-entered          24
21            search term ordered by relevance
           """
22         result=ResultTable()
23         for word in searchString.split():

27             if(len(word)<4): continue
28             word=word.upper()
29             expandedWords=self.wordIndex.expand(word)
               #--don't add unneeded dups
31             try: expandedWords.remove(word)
32             except ValueError: pass
33             expandedString=" ".join(expandedWords)
34             searchString="%s %s" % (searchString, expandedString)
35         normalizedSearchWords=self.wordSubTable.normalizedWordsOf(searchString)

37         tf=1.0/(len(normalizedSearchWords)+1)
38         serviceCnt=self.serviceTable.size()*1.0
39         for word in normalizedSearchWords:
40             wordFreq=self.wordIndex.lookupCount(word)
41             if(wordFreq==0):continue 43             idf=math.log(serviceCnt/wordFreq)
44             tfidf=tf*idf 46             for serviceid in self.wordServiceIndex.lookup(word):
47                 result.add(serviceid,tfidf)
48         for serviceid in result.keys():
49             useFreqFactor=self.serviceTable.getFreqFactor(serviceid)
50             result.add(serviceid, useFreqFactor*tf)
51         return result.byCounts()
```

Fig. 3

COMPUTERIZED SEARCH SYSTEM FOR MEDICATION AND OTHER ITEMS

This application derives priority from Provisional Patent Application Ser. No. 60/807,514, filed on Jul. 17, 2006.

FIELD OF THE INVENTION

The present invention relates generally to the field of data processing, and more particularly to the identification of a desired item residing within a catalog of candidate items.

BACKGROUND OF THE INVENTION

In a health care enterprise physicians, nurses, clinicians and/or other health care providers constantly request or order medications and services in the course of providing patient care. Traditionally orderable item requests have been written by hand by the clinician requesting the medication or service. In order to improve healthcare safety and efficiency, however, computerized provider order entry (CPOE), which requires that orderable items be retrieved from a hospital computer system database containing a list of available orderable items, has been widely proposed as a critically important function.

However at present only a small percentage of hospitals have implemented CPOE. The cultural change involved in persuading physicians and other clinicians to enter orders electronically, rather than by hand, is so disruptive that hospitals are reluctant to undertake such a project. This is primarily due to the considerable extra time consumed in entering the orders via a computer. Instead, to implement CPOE systems, health care enterprises have hired full time clerks specifically to take the hand written orders of physicians and simply enter them into the computer, thereby negating much of the benefit of CPOE.

The time a clinician takes to locate and enter orders for a patient via a CPOE system is dependent on many factors, such as the time taken to find a computer terminal, the time to log on, the time to find the order function screen, the time spent pondering which order might be appropriate, the time spent finding the desired order in the catalog of orders, the time needed to fill out details of the order, the time to resolve conflicts and error messages within the order and the time needed to confirm and sign the order. Two of these factors, finding the desired order and filling out order details, form the bulk of the frustration associated with clinician acceptance of CPOE.

Several methods are typically implemented to allow a clinician to find and select an order from among the order choices available in the CPOE database. One method to allow a clinician to find and select an order from among the order choices available in the CPOE database is searching. A search engine is a program that defines sets of related items that will be created in response to a user input of a string, termed a "search string" or "search term". Typical search methods generally involve simple pattern matching of the search string with the entire orderable item name associated with that orderable item. A simple pattern match searches for the search string as sequential characters in a larger string. If that search string is found, the item is selected. For example a search for "%IDE%" matches "ChlorIDE" "FluorIDE" and "AntIDEpressant".

Searches are typically judged by precision and recall. Precision is defined as the ratio of the number of relevant records retrieved to the total number of records, irrelevant and relevant, retrieved. Recall is defined as the ratio of the number of relevant records retrieved to the total number of relevant records in the database. Simple pattern matching has low recall and low precision. Simple pattern matching has low recall because in order to retrieve an orderable item the search string needs to exactly match the service name, but the exact wording and punctuation of the service name is unknown to the user. For example, a user may wish to enter search pattern "two view chest x-ray" when the orderable item service name is actually "XR: Chest, AP/Lat Views". The pattern does not match and so the computer does not retrieve the service item. To be successful the user must speculate about the ordering and punctuation of the service item, or be trained regarding CPOE system search rules including all of the exceptions, or enter less information in the search request. The latter strategy defeats the purpose of a search which is typically to locate uncommon items not appearing on the commons list. Spelling errors, both in the CPOE system and the search string entered by the user, exacerbate this problem.

Simple pattern matching has low precision because the strategy for improving recall is to include less search information. In the previous example if the user searches for "chest" without the word x-ray, the order may be found. But, there are very many services that match chest, so the user is left with many irrelevant entries. This entails a very high reading load associated with scanning down the list of search results until the correct service item is found. The problem is aggravated by the fact that the results are typically ordered alphabetically rather than by relevancy. This implies that users need to read the entire list to determine that the search failed to return a valid result. Further, the search results may on occasion suggest the use of a sub optimal but similar orderable item that is listed first. For example, a user might choose a service for "XR: Chest, & Ribs, PA/Lat Views" despite the fact that no Rib Views were needed, rather than the more appropriate "XR: Chest, PA/Lat Views", simply because the list was long and the more appropriate choice was lower on the list. Given the ineffective search strategies, most physicians find it faster to write the order by hand and have the unit secretary perform the search.

A need therefore exists to improve the operation of search engines. Any such improvement has great potential for significantly increasing physician satisfaction and acceptance of CPOE systems. A computerized search system constructed according to the principles of the present invention addresses the foregoing deficiencies and related problems.

BRIEF SUMMARY OF THE INVENTION

In accordance with principles of the present invention, a search system finds an order to provide an item. The search system includes a repository including a plurality of records identifying a corresponding plurality of items for order. A record of an individual item for order includes a plurality of related text terms describing order related parameters. A search processor searches the plurality of records to find candidate items for order corresponding to a user entered search term by: identifying and prioritizing candidate items for order in response to a relative frequency of occurrence of the user entered search term in corresponding records of the candidate items for order; and ranking the identified and prioritized candidate items for order in response to a relative frequency of ordering of the identified and prioritized candidate items for use by users. An output processor provides search result data representing the ranked, identified and prioritized candidate items.

BRIEF DESCRIPTION OF THE DRAWING

In the drawing:

FIG. 3 is a pseudo-code listing of an algorithm utilized by the search processor of the system depicted in FIG. 1 according to the present invention.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, search system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by the display processor under the control of the processor. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to the processor. The processor, under control of the executable procedure or executable application manipulates the UI display images in response to the signals received from the input devices. In this way, the user interacts with the display image using the input devices, enabling user interaction with the processor or other device.

Figure 1:
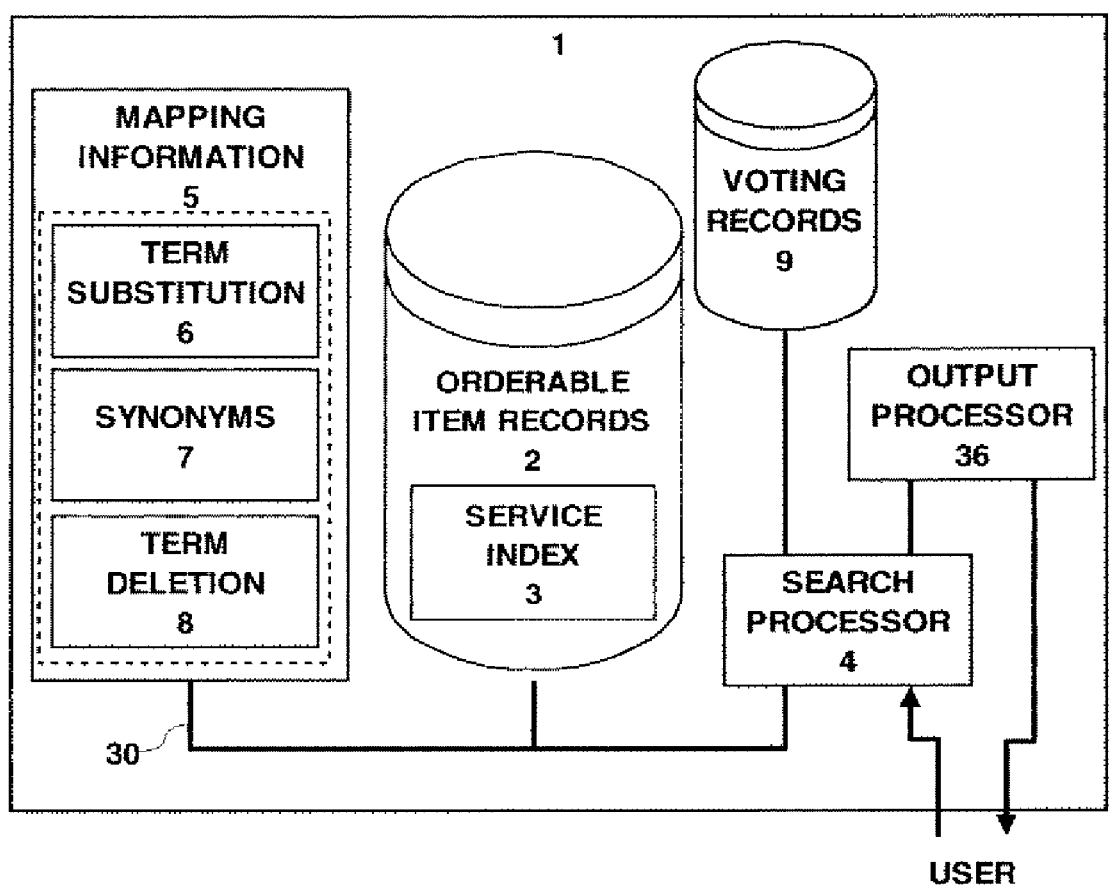
FIG. 1 is schematic diagram depicting a computerized search system constructed according to the principles of the present invention.

FIG. 1 illustrates an embodiment of a computerized search system 1 according to principles of the present invention. The search system 1 finds an order to provide an item. The search system includes a repository 2 including a plurality of records identifying a corresponding plurality of items for order. A record of an individual item for order includes a plurality of related text terms describing order related parameters. For example, the orders may be orders for providing particular medical treatments for a patient and the order related parameters identify: (a) quantity; (b) a route of administering of a medical treatment; (c) a frequency of administering a treatment; and/or (d) a form of medical treatment. The order related parameters may also identify: (a) order urgency; and/ or (b) associated order instructions. The form of medical treatment includes: (a) a package type; (b) a strength of a medical treatment; and/or (c) a concentration of a medical treatment.

A search processor 4 searches the plurality of records to find candidate items for order corresponding to a user entered search term by: identifying and prioritizing candidate items for order in response to a relative frequency of occurrence of the user entered search term in corresponding records of the candidate items for order; and ranking the identified and prioritized candidate items for order in response to a relative frequency of ordering of the identified and prioritized candidate items for use by users. An output processor 36 provides search result data representing the ranked, identified and prioritized candidate items.

The search processor 4 is adapted to perform searches for words and terms appearing in a database 2 via a connection 30 in response to a search string entered by a user. The user entered search term may include a plurality of individual search terms. The database 2 includes records related to items that may be requisitioned or ordered that exist in a catalog of available services and medications, for example. Records in database 2 related to orderable items in the catalog also include associated data records stored in a service index 3. The service index 3 records include labels, categorization, characteristics and order related parameters for each orderable item. Order related parameters can include priority (e.g. "stat"), associated order instructions (e.g. "for pain", "on call to OR", "call with results"), or a relatively abstract grouping of the item for order (e.g. "antibiotic", "cardiology", "common", etc). Order related parameters typically identify a quantity, a route of administration of a medical treatment, a frequency of administering a treatment or a form of medical treatment. The search processor 4 performs searches by querying the service index 3.

The system 1 may also include a repository of mapping information associating an individual term with a plurality of corresponding synonyms. The search processor parses the user entered search string and expands the user entered search string to a corresponding plurality of search terms using the mapping information, described in more detail below.

The system 1 may also include at least one repository of term substitution information including mapping information associating a term with a corresponding term. The search processor parses a search string and substitutes a term for an individual search term by applying the mapping information. In more detail, the term substitution information may include first mapping information associating a term string made up of a plurality of terms with a corresponding single term and second mapping information associating a single term with a corresponding plurality of terms. In one embodiment, the search processor 4 parses a search term and substitutes terms for the search term by firstly applying the first mapping information and secondly applying the second mapping information.

In FIG. 1, a mapping information interface 5 is accessible by the search processor 4 via connection 30 and includes information relating to words and terms that may be encountered by the search processor 4. The information available in the mapping information interface 5 includes word synonyms 7, term substitution information 6 and terms 8 that are to be deleted or ignored. The terms which are to be deleted or ignored typically are short terms which appear often in a large proportion of the orderable item records in the database 2. The search processor 4 excludes these short terms that potentially map to multiple irrelevant terms.

The mapping information interface 5 converts terms in the search string to corresponding normalized terms. For example, a search string including the word "Na" should ideally find orderable items with the term "Sodium" as well as those with the term "Na". The entries in the service index 3 use standardized or normalized terms. The mapping information interface 5 normalizes terms in the search string to the normalized terms appearing in the service index 3. For example, the single term "Sodium" may be used in the service index 3 for the respective records in the orderable item records 2 including terms which are synonyms for sodium, such as "Na". Similarly, the search string terms are normalized so that the normalized synonym for a term is used to perform a search. Continuing the example, synonyms for the term "Sodium", e.g. "Na", in a search string are converted to the single term "Sodium". Synonym information 7 is accessed to check whether the respective terms in the search string correspond to a standardized or normalized term in the service index 3. If so, then those terms in the search string are replaced with the normalized or standardized term before a search of the service index 3 is performed. In this manner, searches for a term having synonyms will find the respective corresponding records in the service index 3 and orderable item records database 2, despite use of different synonyms, thus increasing the recall of a search. Such a search may still include a large number of items for a clinician to review, however.

Once the search has been performed, the search processor 4 identifies and prioritizes individual candidate items for presentation in an order proportional to a number of occurrences of the user entered search term relative to a number of terms in a corresponding record of an individual candidate item for order. That is, the search processor 4 determines a relative frequency of occurrence of an individual user entered search term in a corresponding service index 3 record of a candidate item for order for each term of the plurality of individual search terms. The search processor 4 then sums data representing the relative frequency of occurrence of individual user entered search terms for each term in the search string to provide summed data corresponding to the candidate item. Then the search processor 4 ranks the identified and prioritized candidate items for presentation in order in response to the summed data. Candidate items having a relatively higher sum are ranked higher than those having a relatively lower sum. The search processor 4 further ranks those candidate items using data representing the relative frequency of ordering of the identified and prioritized candidate items for use by users. Candidate items ordered relatively more frequently are ranked higher than those ordered relatively less frequently. In one embodiment, the search processor weights the summed data relative to the data representing the relative frequency of ordering of the identified and prioritized candidate items for use by users, to provide data indicating ranking of the identified and prioritized candidate items.

Referring to FIG. 3, the search processor 4 (FIG. 1) performs the term search function according to an algorithm 24 represented by pseudo-code illustrated in FIG. 3. The algorithm 24 is adapted to examine the individual terms or words residing in the service index 3 and compare them to a request in the form of a search term entered by a user of the system 1. Records indicating a match are selected as candidate orderable items. Lines 37 through 44 of the algorithm 24 define a term frequency-inverse document frequency (TF-IDF) technique utilized to weight candidate orderable items. It is based on the observation that an identified candidate item is relatively more important if it has more occurrences of a search term than a candidate item that has fewer occurrences, and an identified candidate item is more important if it is one of a relatively few available orderable items including the search term than if it is one of relatively many available orderable items including the term.

In one embodiment, the weight of the individual candidate items, is assigned according to the following equations:

$$tf = \frac{n_i}{\sum_k (n_k)} \quad (1)$$

$$Tf * idf = tf \cdot \log\left(\frac{|D|}{|d_j \supset t_i|}\right) \quad (2)$$

where:
tf=the term frequency
$n_i$=the number of occurrences of the term in the search string
$\Sigma_k (n_k)$=the number of terms in the search string
|D|=number of orderable items in the service index
$|(d_j \supset t_i)|$=number of orderable items in which term appears
Tf*idf=the weight or importance of the candidate item.

The ranked score of any candidate orderable item is the sum of the tf*idf weights for the respective terms appearing in the search string.

Orderable item descriptions or labels are similar to typical documents in that they contain multiple words which act as a vector representation of the search object. Orderable items differ from typical documents, however, because the typical document vector is longer and more complex and usually contain relatively many words as well as words that are often repeated many times within a single document. However, the tf-idf formula is appropriate for searching orderable items because the formula attempts to determine the relative weight or importance of a word according to Zipf's law, which states that the frequency of any word is inversely proportional to the rank of the word in a frequency table. Stated differently, the frequency of the second most frequent word appearing in an index table item description or title occurs about twice as often as the fourth most frequent word, for example.

The system 1 (FIG. 1) improves on ordinary tf*idf weighting in several advantageous ways. Due to the typically brief description or title of each orderable item, the search result produced by the search processor 4 for single terms and for multiple terms produces many orderable items having the same weight. This is because there is relatively little information in the orderable item labels and in the typical search strings so there is often no way to differentiate between orderable items based on words alone. To address this problem, a service popularity weight is considered and factored into the results produced by the search processor 4. The additional service popularity information is stored in a voting records data base 9 and supplied to the search processor 4 in the form of a vote or preference for a given orderable item. The voting is achieved by at least one of: (a) selection of an item for order in normal use, i.e. the more often the orderable item is ordered, the higher the popularity and the higher the service popularity weight; and (b) manual adjustment of priority weighting of that item for order. That is, a vote may be produced if an item or service is ordered, or ordered above a threshold frequency, by other users; or the vote may be based on a predetermined hospital preference for a particular orderable item. The search processor 4 alters the search result ranking based on voting mechanisms for the items for order.

The service popularity weight is added to the ranked score with a weight equal to that of an individual search term match. Service popularity separates items of otherwise equal weight without interfering with the importance of the actual terms appearing in the search strings entered by the user. For example, if the user enters the single search term of "chest", she may expect to receive a list of all orderable items that relate to the concept of chest. This list is ordered with the most frequently ordered item at the top of the list. In other words the search returns the orderable items ranked according to what the user probably wants to actually order.

If the user adds more information to the search string, e.g. enters a search for "chest ct" then she receives a list of orderable items that have the terms "chest" and/or "ct" ordered according to the orderable items that have both concepts listed first, followed by those orderable items with the term "chest" since "chest" is a more specific term having a higher idf than the term "ct". The search results also display those items with only "ct". If there are multiple items that have the terms "chest" and "ct" such as "CT: Chest with IV Contrast" and "CT: Chest without Contrast", then the more popular chest ct orderable items are listed first. In order to achieve ranking that includes the service popularity factor, service popularity is normalized against other services and placed on a logarithmic scale that matches the idf weight scale. Normalization ensures that effect of voting data does not overpower the importance of the actual search terms, while preserving the advantage that is inherent in a voting system, namely, that a vote for orderable item A (i.e. by ordering orderable item A) also causes items B and C to become slightly less popular.

A system 1 for searching for a particular orderable item within a catalog of orderable items requires the following actions. An index of characteristic words associated with orderable items is created. This index resides in the catalog of orderable items. In FIG. 1, the service index 3, within the database 2 of orderable items, includes this index. A user creates a search phrase that includes words likely to be present in a description of a particular orderable item. This search phrase is supplied to the search processor 4. Words appearing in the service index 3 of characteristic words are associated with mapped words that share similarities with the characteristic words. The information in the mapping information store 5 include substitute term information 6, and synonym information 7 that include words that share similar similarities with the characteristic words. The search phrases is parsed and mapped words from the mapping information store 5 are substituted for at least some of the words in the search phrase. A list of orderable items containing the substituted mapped words is then created. The search processor 4 uses the revised search string to search for matches in the records in the service index 3. The list of orderable items is then ranked according to a frequency of ordering particular orderable items by previous users of the catalog of orderable items. Information from the voting records 9 is used by the search processor 4 to rank the list of candidate orderable items.

Figure 2:
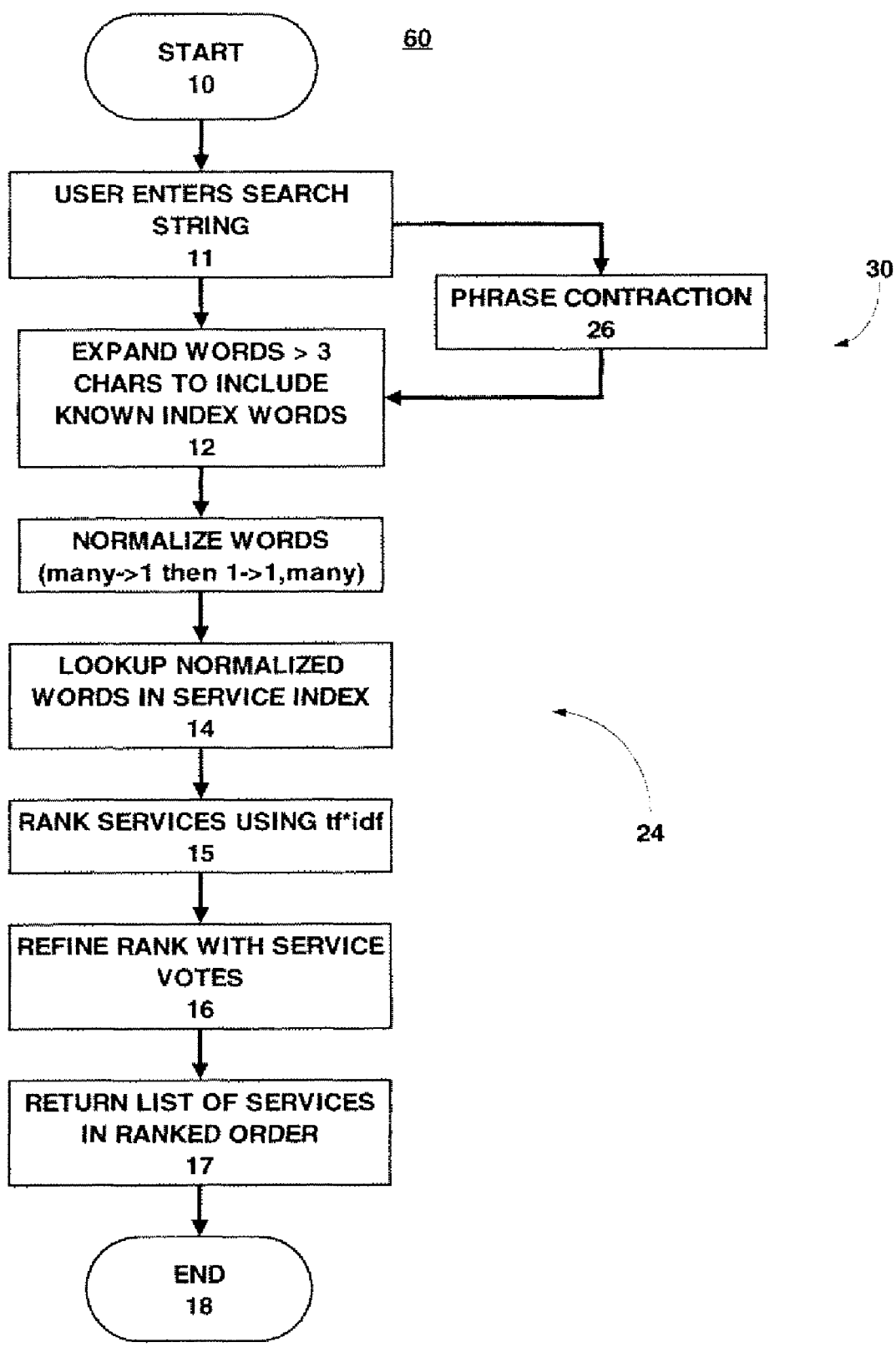
FIG. 2 is a flow chart depicting the data flow within the search processor of the system depicted in FIG. 1 according to the present invention.

Referring to FIG. 2, the data manipulation steps performed by the search processor 4 (FIG. 1) via an executable procedure 60 which includes the search algorithm 24 (FIG. 2) may be better appreciated. The executable procedure 60 is initialized at step 10. A user may enter a search string for candidate orderable items at step 11 via any suitable user interface (UI). The user interface includes one or more display images enabling user interaction with the search processor 4. The search string entered by the user may include a diagnosis code associated with a candidate orderable item, a medical condition associated with a candidate orderable item as well as a medical problem associated with a candidate orderable item. From this information, the search processor 4 may rank the identified and prioritized candidate items for order in response to: (a) a diagnosis code associated with the candidate order; (b) a medical condition associated with the candidate order; and/or (c) a medical problem associated with the candidate order.

As described above, the search processor parses the user entered search term and expands the user entered search term to a corresponding plurality of search terms using the mapping information 5 (FIG. 1). For example, the user may enter the search term "C Diff", which may correspond to any of a number of orderable items residing in the service index 3. Step 12 initiates the word expansion function of the search algorithm 24. The mapping information 5 is accessed to retrieve term substitution information 6, synonym information 7 and term deletion information 8 used by this function. The word expansion function replaces the search term with multiple terms. For example a search for a search term "PT" is ambiguous in that it matches both orderable items for "Physical Therapy" and orderable items for "Protime". Term substitution information 6 and synonym information 7 include respective entries indicating that both orderable items are commonly abbreviated as PT. In order to provide the clinician with candidate orderable items which are most likely desired, the word expansion function 12 expands the search to include both orderable items "Physical Therapy" and "Protime".

Word expansion is also useful for mapping simple term substitutions where a search term may map to a service indexed with two different words. For example, "CXR" is a common abbreviation for "chest X-ray" that is mapped to the equivalent indexed words "X-ray" and "Chest". Synonym information 7 includes respective entries which relate a search term to a normalized or standardized term. For example, an entry in the synonym information 7 relates the term "CXR" to "X-ray" and another entry relates the term "CXR" to "Chest".

Step 12 also expands search terms with four or more letters to matching indexed words. Expanding words with three or less letters exponentially decreases the precision of abbreviations such as K for potassium or Na for Sodium and acronyms such as PO to represent oral, for example, while expanding search terms having four or more characters greatly increases recall, particularly since long words often are misspelled.

Thus, any word appearing in the search string that contains more than three letters is expanded to include all words residing in the service index 3 (FIG. 1) that begin with those four or more letters. Term substitution information 6 and synonym information 7 is accessed to retrieve entries matching the initial letters of the search term. Associated normalized or standardized terms having the same initial letters is retrieved and used for searching the service index 3. For example, the word "C" appearing in the search string does not contain more than three letters, and so is not expanded. However, the term "Diff" does contain four or more letters and so is expanded. That is additional search terms are added to the search which begin with the letters "Diff". The service index 3 may contain, for example, the words "Difficile", "Diffusion" and "Differential", thereby expanding the total number of search terms searched to five when including the original user entered the term "C Diff".

Prior to step 12, the phrase being searched is examined by a phrase contraction function 26. The phrase contraction function 26 replaces a sequence of words with an equivalent single term. This function is useful whenever a term is indexed under a single term but typical users may employ searches that contain multiple terms. For example, the phrase "X Ray" (with a space) is contracted to "XRay" (without a space) and "cat scan" is contracted to CT. The phrase contraction function also employs a form of protection against improper word expansions that would otherwise be performed at step 12. For example, the phrase contraction function recognizes that in a search for the orderable item "consult pt", the term "consult" narrows the ambiguous term "pt" to the concept of "physical therapy" and eliminates the possibility that the user was searching for the orderable item "Protime". The limitation or contraction of the term "consult_pt" to "consult physical therapy" prevents the term "pt" from being subsequently expanded into protime. For this reason the phrase contraction step 26 occurs before word expansion. The use of relatively few phrase contractions and word expansions enables precise search returns from a wide variety of user defined search strings.

After the word expansion step 12 has created the revised search string appearing at line 34 of the search algorithm 24 (FIG. 2), the words appearing in the revised search string are normalized at step 13. In other words, once step 12 has created an enlarged list of words that appear in the service index 3 (FIG. 1), the normalization step 13 removes phrases or segments that may be associated with many different word entries in the service index 3 but which are not actually words contained in the mapping information interface 5, and retains those words that are associated with a single word entry in the mapping information interface 5. In the example user defined search string "C Diff", the normalization step 13 retains an expanded word such as "clostridium" because it appears in the mapping information interface 5 in the phrase "clostridium diff". However, the user entered word "diff" is itself discarded because "diff" is associated with many words but is not itself a word appearing in the mapping information interface 5, while the expanded terms with which "diff" is associated in the mapping information interface 5, such as "Difficile", "Diffusion" and "Differential" are retained.

After the normalization process is completed at step 13, step 14 begins the search for the normalized words appearing in the service index 3 (FIG. 1). In the foregoing example of the search string "C Diff" the words actually being searched are "clostridium", "difficile", "diffusion" and "differential". None, one or more orderable items might be returned for each word. For example, "difficile" might match the single orderable item "C difficile toxin", "diffusion" might match the single orderable item "MRI: Brain(Diffusion Weighted)" and "Differential" might match the single orderable item "CBC w/Differential".

Given the existence of the preceding matches, step 15 ranks the returned matches with the tf*idf formula as shown at line 44 of the search algorithm 24. The higher the ranking number returned by the tf*idf formula, the greater the likelihood that the orderable item is the item originally desired by the user when the original search string was entered. For example, the orderable item "C Difficile Toxin" might receive a relatively high rating of 2.7 because two words, "C" from the original search string and "Difficile" from the expanded search string are both present. The orderable item "MRI: Brain (Diffusion Weighted)" might receive an intermediate rating of 1.9 because of matching only the one search term "diffusion", and the orderable item "CBC w/Differential" might receive a lower rating of 1.7 because the single matched word "differential" is less specific than the term diffusion.

The raw ranked search result ratings produced at step 15 are refined with the aid of service vote popularity data at step 16 as seen at line 49 of the search algorithm 24. The revised ranking for the orderable item "C Difficile Toxin" might be increased to 3.8 if it is a somewhat commonly ordered service. "CBC w/Differential" might increase to 3.1 if it is a very commonly ordered procedure, and "MRI: Brain (Diffusion Weighted)" might be ranked at 2.8 if it is a service that is not commonly ordered. The final list of orderable items returned to the user at step 17 is, in this particular example, in the same order as the rankings produced by step 16. The search is therefore completed at step 18 and the results are forwarded to the output processor 36 for display to the user.

While the system 1 has been described with reference to specific embodiments, many variations are possible. For example, the system 1 is usable to improve the rank ordering of any computer application that has a catalog of parts or services, such as automobile parts catalog, list of services available from a maintenance company, or a retail store that maintains a list of products. A computer application can include code or machine readable instruction for implementing predetermined functions including those of an operating system, healthcare information system or other information processing system, for example, in response user command or input.

What is claimed is:

1. In a health care enterprise, a computerized provider order entry system for receiving one or more search terms from a health care provider and finding an order for providing a medication or medical service related to the one or more search terms, comprising:

a repository including a plurality of records identifying a corresponding plurality of medications or medical services available for order, a record of an individual medication or medical service available for order including a plurality of related text terms describing order related parameters, including terms identifying a treatment and at least one of: (a) a diagnosis code associated with the medication or medical service available for order, (b) a medical condition associated with the medication or medical service available for order, and (c) a medical problem associated with the medication or medical service available for order;

a search processor for searching said plurality of records to find candidate medications or medical services available for order corresponding to the one or more health care provider entered search terms by:

determining a relative frequency of occurrence of respective ones of the one or more search terms in the related text terms of corresponding records of candidate medications or medical services available for order;

summing data representing the relative frequency of occurrence of the respective ones of the one or more search terms to provide data representing a summed relative frequency of the one or more search terms in corresponding records of candidate medications or medical services available for order;

identifying and prioritizing candidate medications or medical services available for order in response to the summed relative frequency of occurrence of said health care provider entered search terms in corresponding records of said candidate medications or medical services available for order; and ranking said identified and prioritized candidate medications or medical services available for order in response to a relative frequency of ordering of said identified and prioritized candidate medications or medical services available for use by health care providers;

wherein said search processor alters search result ranking based on voting mechanisms for said medications or medical services available for order, said voting achieved by at least one of (a) selection of an item for order in normal use and (b) manual adjustment of priority weighting of that item for order; and an output processor for providing search result data representing said ranked, identified and prioritized candidate medications or medical services.

2. A system according to claim 1, wherein said search processor weights said summed data relative to said data representing said relative frequency of ordering of said identified and prioritized candidate medications or medical services for order, to provide data indicating ranking of said ranked, identified and prioritized candidate medications or medical services.

3. A system according to claim 1, wherein said orders are orders for providing particular medical treatments for a patient and said order related parameters identify at least one of, (a) quantity, (b) a route of administration of a medical treatment, (c) a frequency of administering a treatment and (d) a form of medical treatment.

4. A system according to claim 3, wherein said form of medical treatment comprises at least one of, (a) a package type, (b) a strength of a medical treatment and (c) a concentration of a medical treatment.

5. A system according to claim 1, wherein said orders are orders for providing particular medical treatments for a patient and said order related parameters identify at least one of, (a) order urgency and (b) associated order instructions.

6. A system according to claim 1, wherein said search processor identifies and prioritizes individual candidate medications or medical services available for order proportional to a number of occurrences of said user entered search term relative to a total number of terms in a corresponding record of an individual candidate item for order.

7. A system according to claim 6, wherein said search processor identifies and prioritizes individual candidate medications or medical services available for order using:

$$tf = \frac{n_i}{\sum_k (n_k)}$$

$$Tf * idf = tf \cdot \log\left(\frac{|D|}{|d_j \supset t_i|}\right)$$

where:
tf=the term frequency
$n_i$=the number of occurrences of the term in a search string
$\Sigma(n_k)$=the number of terms in a search string
|D|=number of orderable medications or medical services
$|(d_j \supset t_i)|$=number of orderable item records in which term appears
Tf*idf=the weight or importance of the term.

8. A system according to claim 1, further comprising:
a repository of mapping information associating an individual term with a plurality of corresponding synonyms; wherein
said search processor parses said healthcare provider entered search terms and, if a search term in the one or more search terms is in the repository of mapping information, expands said healthcare provider entered search term to a corresponding plurality of search terms using said mapping information.

9. A system according to claim 1, further comprising at least one repository of term substitution information comprising:
first mapping information associating a term string comprising a plurality of terms with a corresponding single term; and
second mapping information associating a single term with a corresponding plurality of terms; wherein:
said search processor parses said healthcare provider entered search terms and substitutes a corresponding single search term for a plurality of said one or more search terms by applying said first mapping information and substituting a plurality of search terms corresponding said single search term by applying said second mapping information.

10. A system according to claim 1, further comprising:
at least one repository of term substitution information comprising mapping information associating a term with a corresponding term; and
said search processor parses a search term in the one or more search terms and substitutes an associated corresponding term for said search term by applying said mapping information.

11. A system according to claim 10, wherein:
said search processor searches for text terms describing order related parameters beginning with the same letters of an associated corresponding term in said search terms.

12. A system according to claim 11, wherein said search processor identifies and prioritizes individual candidate medications or medical services for order proportional to the number of occurrences of said healthcare provider entered search terms relative to a total number of terms in the corresponding record of an individual candidate item for order.

13. A system according to claim 10, wherein said search processor excludes short terms that potentially map to multiple irrelevant terms.

14. A system according to claim 1, further comprising:
a repository of first mapping information associating an individual term with a plurality of corresponding synonyms; wherein
said search processor parses said one or more healthcare provider entered search terms and expands respective healthcare provider entered search terms to a corresponding plurality of search terms using said mapping information.

15. A system according to claim 14, further comprising
at least one repository of term substitution information comprising:
second mapping information associating a term string comprising a plurality of terms with a corresponding single term and
third mapping information associating a single term with a corresponding plurality of terms; wherein:
said search processor parses a search term in the one or more healthcare provider entered search terms and substitutes a corresponding plurality of terms for said search term by applying said second mapping information and substitutes a single term for a corresponding plurality of terms by applying said third mapping information.

* * * * *